Dec. 9, 1952 S. R. PHELAN Plant Pat. 1,152
ROSE PLANT
Filed Aug. 3, 1950
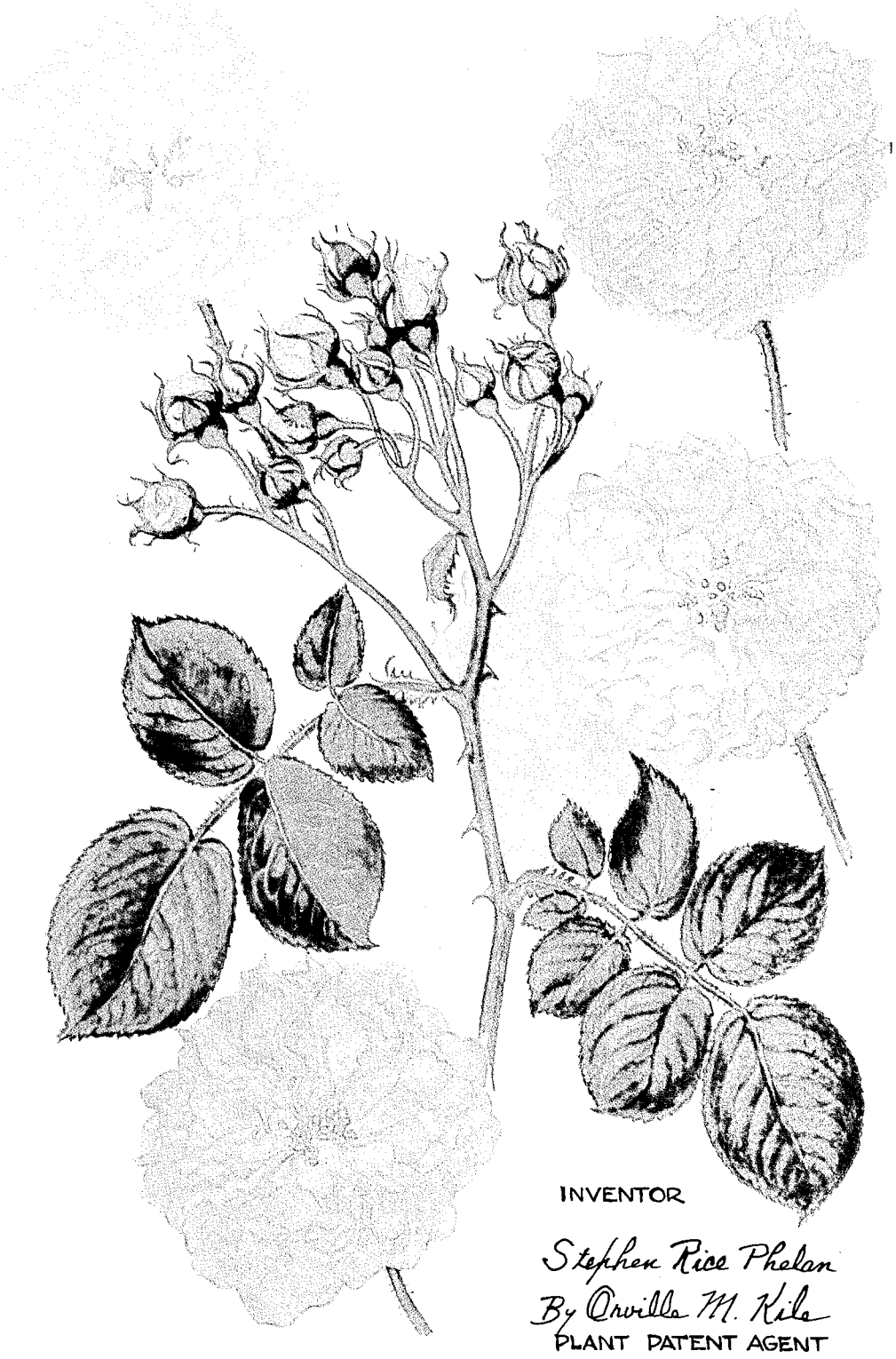

Patented Dec. 9, 1952

Plant Pat. 1,152

UNITED STATES PATENT OFFICE 1,152

ROSE PLANT

Stephen Rice Phelan, Memphis, Tenn.

Application August 3, 1950, Serial No. 177,477

1 Claim. (Cl. 47—61)

My present discovery relates to a new and improved variety of hybrid China rose plants, the novel features of which include particularly the presence of several colors of flowers on a single bush at the same time, one color being a wisteria blue not, I believe, heretofore known in roses at their opening.

The new variety originated as a sport of one of my own unnamed seedlings and was discovered and asexually reproduced by me in my gardens in Memphis, Tennessee, where I have reproduced this variety both by division and by self-rooted cuttings of branches. Reproduction by cuttings has now been repeated through several generations and the latest generation seems to be identical with the earlier generations and with the original sport. Most outstanding among its characteristics are its great vigor, its numerous blooms, intense perfume, hardiness, resistance to disease and insects, and the color pattern of its blooms which includes five types. Its growth is so vigorous that it can well be used as understock and no budding is necessary when growing it for its own blooms.

During May 1951, in my garden in Memphis, Tennessee, there were 18 such rosebushes having several hundred blooms each. Every one was at least five feet tall. Half were one year old, grown on their own roots from a single parent bush, and were identical with the parent in all respects, including plant parts, color, pattern and form of flowers, and their manner of flowering. The other half were own-root plants grown from random cuttings taken from the first half, or from previously-raised and more mature bushes of the same kind. Without exception, the new plants and flowers are exactly like the parents and grand-parents. The colors and mixture of colors are the same as in the parent—the resemblance so evident that one is not confused by the varying proportions.

The accompanying illustrations show a cluster of buds with foliage, and four specimens of typical blooms in as near the natural colors as the artist could make them. It must be understood, however, that various other shades and tints of these typical colors occur either at the opening stage of the flower or later.

The full white type is not shown because of space limitations and the further fact that it can be described in general terms. Also the white of the mixed specimen is the same as in the all-white specimen, being a pure bright white. The form and petalage of the all-white is the same as for the specimens shown.

Following is a detailed description of the plant and flower of my new rose variety. Color plate references are to Ridgway's Color Standards and Nomenclature and the the Color Charts of the Royal Horticultural Society of London. Where no plate references are given the usual dictionary meaning of the term is intended.

*The plant*

Blooming habit: Very profuse bloomer—an average mature bush having over 1,000 blooms and the larger bushes upward of 1,500 blooms in a single season, which is 1 to 2 months in duration. In the year 1950 one of my bushes had 500 buds and it was at that time only six months old from the cutting.

Growth habit: Extremely vigorous, attaining the height of an average man in a single season. Bush becomes 6 feet or more tall, sometimes with a slight tendency to climb. Variety requires no budding, since in a year's time it produces large blooming bushes from cuttings.

Form: Very tall, erect and symmetrically radiating bush, sometimes with tendency to climb. Canes free, straight and with few branches. Branchlets parallel, alternate and regular from and radiating around canes. Makes an excellent shrub or hedge rose.

Stems and canes: Strong, straight and thick. Dull green, with bright green branchlets usually with reddish tips. Branchlets approximately 1 foot long. A few medium-sized thorns appear low on canes at intervals of about 1 inch and irregularly spaced around canes. Branchlets have occasional prickles and the peduncle usually has numerous small reddish prickles and bristles.

Foliage: Pinnately compound; mostly with 5 leaflets, sometimes 7.

*Quantity.*—Abundant; freely distributed from top of bush to within about a foot of the ground.

*Shape.*—Leaflets elliptical to orbicular, with small acute apex and rounded base. Edges medium serrate-dentate; not much flexed.

*Color.*—Dark green (approximately Dark Cress Green, Ridgway's Pl. XXXI) on upper surface; under surface light grayish-green with red glands. Edge often reddish tinged. Young leaves light green with slight reddish margin.

*Texture.*—Thick; leathery.

*Aspect.*—Wrinkled; dull; downy uncolored hairs on under surface.

*Size.*—Small to medium. Terminal leaflet approximately 1¼ to 1½ inches in diameter.

*Rachis.*—Upper surface grooved; reddish, particularly at base. Under surface has a few bristles and prickles. Base is exceptionally wide and usually reddish tinged.

*Stipules.*—Medium to wide; adnate; pectinate; have long points extending at approximately a 45-degree angle.

*Disease and insect resistance.*—Very resistant to mildew, blackspot and other diseases common to roses, also resistant to insects. Superior to Pink Radiance in these respects when grown nearby and under similar conditions. In fact, equal to Multiflora grown nearby and originally intended for budding stock but not needed because of the exceedingly vigorous growth of my new variety.

*Hardiness.*—Very hardy in this climate where it has been tested.

*Bracts.*—Numerous bristle-like, brownish-red bracts appear along stem. Edged with reddish glands.

*The flower*

Bud:

*Size.*—Small, ½ to ¾ inch long.

*Shape.*—Ovoid.

*Opening.*—Opens well to a medium-sized, cupped bud which grows in size even after opening.

*Color at early opening.*—Light greenish-white to white on outside, with purplish-red flushes.

*Calyx and sepals.*—Calyx is composed of five sepals attached at base (Lettuce Green, Royal Horticultural Society 861, p. 176; Ridgway, Pl. V). Sepals moderately long and spear-shaped, each having 5 to 7 fringing appendages extending from the two side edges and a moderately long foliaceous appendage from apex. Sepals recurve early; persist after petals fall.

Bloom:

*Borne.*—In clusters averaging 7 blooms, with long stems or pedicels. These clusters emanate from the main stems, usually in the axil of the leaf or bract, and are true cymes—the white center flower being the first to open. Since the stems are long, the clusters make good cut flowers, each cluster being almost a bouquet in itself.

*Form.*—At first full, then petals loosely cupped, later becoming almost spherical, and at maturity becoming very loosely flat cupped. Outer petals have some tendency to roll outward at their tips.

*Size.*—Average size is 2¼ to 2½ inches in diameter, with some few attaining a 3-inch diameter in good years and when bushes are drastically pruned.

*Petalage.*—75 to 100 petals.

*Quantity of bloom.*—The average is 1,000 to 1,500 blooms to a bush in one season.

*Fragrance.*—Distinctive. Very strong but pleasant centifolia odor.

*Color.*—The color pattern of the bloom of my new rose variety falls into 5 types, three of which may be called virgin or opening colors—the other two developing from the original three. The types are indicated as follows:

1—brilliant white, and perhaps some few pink blooms.

2—reddish purple (Tyrian Purple, 727/3, Royal Horticultural Society), with edging of Light Wistaria Blue (640/1, Royal Hort. Society, or Pl. XXIII, Ridgway's), which is very close to true blue.

2(*a*)—changing from type No. 2 to varying shades of pink tending to the lavender side, with petals often edged with white or very light Wistaria Blue.

2(*b*)—changing from type No. 2(*a*) to Orchid Purple (31/2, Royal Horticultural Society), with petals edged in Light Wistaria Blue to Wistaria Blue (640/1, Royal Horticultural Society, or Pl. XXIII, Ridgway's), to Pale Wistaria Blue (Pl. XXIII, Ridgway's). Light true blue may tone edges and inside surface of petals.

3—one-fourth to one-half of bloom brilliant white, the rest as given in type No. 2. [Actually a few blooms occur which are flag-striped: with Tyrian Purple as in No. 2 above, with Light Wistaria Blue edging; white as in No. 1; and No. 2(*b*) blue type.] The Tyrian Purple or red of this type changes as in types Nos. 2(*a*) and 2(*b*).

All types may appear on the bush at the same time and all persist for several days. Types 1, 2 and 3 are the virgin or opening colors which appear when the blooms open, while types 2(*a*) and 2(*b*) are the changes which come from these three virgin types. Pink sometimes appears in the virgin or opening type as well as in the changes.

These are the principal patterns of color but are not necessarily all the colors and combinations found. All colors, particularly the virgin colors, are usually very bright and vivid.

All color types end up a dull white as real fading and wilting wreak their toll. This, however, is an entirely different white from the brilliant white virgin or opening color.

Petals:

*Size.*—1 to 1¼ inches long.

*Texture.*—Medium thickness; soft, with surfaces satiny.

*Shape.*—Outside and intermediate petals obcordate. Inside petals narrowly obovate.

*Persistence.*—Fairly persistent attachment and flowers last well both on bush and as cut flowers.

Reproductive organs:

*Pistils.*—Medium size; few; loosely bunched in center of flower. Styles — uneven lengths; slender; half the length of filaments. Stigmas — very light yellowish-green, usually with dark red at entrance.

*Stamens.*—Moderate number, arranged about pistils in loose bunch of uneven, irregular lengths. In some blooms ring is visible Lemon Yellow (p. 4, vol. 1, Royal Horticultural Society, Plate IV, Ridgway's). Anthers—medium size; open at various times. Buttercup Yellow (p. 5, vol. 1, Royal Horticultural Society). Pollen—sparse; gold color.

*Ovaries.*—Enclosed in calyx.

*Hips.*—Ovoid, with inconspicuous neck. Medium green, often with small reddish streak or red flushes on sun side; moderately smooth; walls thin. Not many ripen.

Having thus disclosed my discovery, I claim: The new and distinct variety of hybrid China rose plant, substantially as herein described and illustrated, characterized particularly by its very vigorous and rapid growth, enabling the variety to be used without budding and as an understock; its resistance to disease and insects; its symmetrical bush form; its extremely floriferous blooming habit; its rough Rugosa-type leaves;

its long-stemmed flower clusters of cyme formation; and its medium-sized flowers having intense perfume and a variety of colors including among others, white, pink, Tyrian purple, orchid purple, lavender and wisteria blue, the latter color being particularly distinctive among roses.

STEPHEN RICE PHELAN.

No references cited.